US008842897B2

(12) United States Patent
Hezel et al.

(10) Patent No.: US 8,842,897 B2
(45) Date of Patent: Sep. 23, 2014

(54) QUANTIFICATION OF THE IMAGE QUALITY FOR THE MOTION-SYNCHRONIZED CAPTURE OF A CROSS-SECTIONAL TOMOGRAPHIC PICTURE OF AN OBJECT

(75) Inventors: Fabian Hezel, Siegburg (DE); Thoralf Niendorf, Aachen (DE)

(73) Assignee: Max-Delbrueck-Centrum fuer Molekulare Medizin (MDC), Berlin (DE)

( * ) Notice: Subject to any disclaimer, the term of this patent is extended or adjusted under 35 U.S.C. 154(b) by 410 days.

(21) Appl. No.: 13/146,336

(22) PCT Filed: Mar. 5, 2010

(86) PCT No.: PCT/EP2010/001381
§ 371 (c)(1),
(2), (4) Date: Sep. 14, 2011

(87) PCT Pub. No.: WO2010/099973
PCT Pub. Date: Sep. 10, 2010

(65) Prior Publication Data
US 2012/0045104 A1    Feb. 23, 2012

(30) Foreign Application Priority Data

Mar. 5, 2009  (DE) .................. 10 2009 011 382

(51) Int. Cl.
| | |
|---|---|
| G06K 9/00 | (2006.01) |
| A61B 5/055 | (2006.01) |
| G06T 11/00 | (2006.01) |
| G06T 7/00 | (2006.01) |
| A61B 5/00 | (2006.01) |
| A61B 6/03 | (2006.01) |

(52) U.S. Cl.
CPC ................ *G06T 7/0012* (2013.01); *A61B 6/03* (2013.01); *G06T 2207/10072* (2013.01); *A61B 5/055* (2013.01); *G06T 11/008* (2013.01); *G06T 2207/30168* (2013.01); *A61B 5/7285* (2013.01); *G06T 2207/30048* (2013.01)
USPC .......................................... 382/131; 382/128

(58) Field of Classification Search
CPC .......... G06T 2207/30048; G06T 2207/30168; G06T 7/0012
USPC .................................... 382/128, 131
See application file for complete search history.

(56) References Cited

U.S. PATENT DOCUMENTS

| | | | | |
|---|---|---|---|---|
| 4,326,252 A | * | 4/1982 | Kohno et al. | 378/14 |
| 4,831,528 A | * | 5/1989 | Crawford et al. | 382/131 |
| 4,878,169 A | * | 10/1989 | Toner et al. | 382/131 |
| 4,939,646 A | * | 7/1990 | Essinger et al. | 382/128 |
| 5,170,347 A | * | 12/1992 | Tuy et al. | 345/419 |
| 5,909,602 A | * | 6/1999 | Nakai et al. | 399/8 |
| 6,256,404 B1 | * | 7/2001 | Gordon et al. | 382/131 |
| 6,265,874 B1 | * | 7/2001 | McGee et al. | 324/312 |
| 6,385,332 B1 | * | 5/2002 | Zahalka et al. | 382/128 |
| 6,463,167 B1 | * | 10/2002 | Feldman et al. | 382/128 |
| 6,798,906 B1 | * | 9/2004 | Kato | 382/176 |
| 6,947,040 B2 | * | 9/2005 | Tek et al. | 345/420 |
| 6,980,845 B1 | * | 12/2005 | Alsop | 600/410 |
| 2003/0095121 A1 | * | 5/2003 | Huseyin et al. | 345/423 |
| 2006/0078182 A1 | * | 4/2006 | Zwirn et al. | 382/128 |
| 2008/0260226 A1 | * | 10/2008 | Moriya | 382/128 |
| 2009/0046909 A1 | * | 2/2009 | Rutenberg et al. | 382/128 |
| 2011/0105890 A1 | * | 5/2011 | Niendorf et al. | 600/413 |
| 2012/0045104 A1 | * | 2/2012 | Hezel | 382/131 |
| 2013/0300410 A1 | * | 11/2013 | Niendorf et al. | 324/307 |

FOREIGN PATENT DOCUMENTS

JP    2008054738 A  *  3/2008

OTHER PUBLICATIONS

Becker,Frauenrath-,Hezel,Krombach,Kremer,Koppers,Butenweg,Goemmel,Utting,Schulz-Menger,Niendorf,Comparison of left ventricular function assessment using phonocardiogram- and electrocardiogram-triggered 2D SSFP CINE MR imaging at 1.5 T and 3.0 T, 2009,1344-1355, EUR Radiol (2010) 20, European Society of Radiology 2010,online.

Manduca,McGee,Welch,Felmlee,Grimm,Ehrman,Autocorrection in MR Imaging: Adaptive Motion Correction without Navigator Echoes,Sep. 14, 2000.904-909-,06-2000,RSNA 2000.

Sachs,Meyer,Hu,Kohli,Nishimura,Macovski,Real-Time Motion Detection in Spiral MRI Using Navigators,Nov. 1994,639-645,MRM 32,Information Systems Laboratory,Dept of Electrical Engineering, Stanford University, Stanford,CA.

Larson,Kellman,Arai,Hirsch,McVeigh,Li,Simonetti,Preliminary Investigation of Respiratory Self-Gating for Free-Breathing Segmented Cine MRI,Aug. 16, 2004,159-168,Magnetic Resonance in Medicine 53, 2004 Wiley-Liss,Inc, online.

Marziliano,Dufaux,Winkler,Ebrahimi,Perceptual Blur and ringing metrics: application to JPEG2000,2004, 163-172, Signal Processing: Image Communication 19, ELSEVIER, Switzerland.

Prest, Phillips,Nikitin, Langton,Cleland, Automated left ventricular cardiac MRI segmentation, quantification and visualization using a radial-ray approach, 2004,1120-1125, CARS and ELSEVIER Switzerland.

* cited by examiner

*Primary Examiner* — Gandhi Thirugnanam (74) *Attorney, Agent, or Firm* — Andrew Wilford (57) ABSTRACT

The invention relates to a method for the quantification of the image quality of at least one tomographic picture of an object, wherein at least one tomographic cross-sectional image is produced using a cross-sectional imaging method, in particular a magnetic resonance tomography method. As a measure of the image quality in a cross-sectional image, an image detail is measured, in particular the width of a boundary between two adjacent areas is determined, in particular with the signal intensity remaining constant in each such area, in particular said signal intensity remaining constant at least within predetermined/predeterminable boundaries. The invention further relates to a method for the motion-synchronized capture of at least one tomographic picture of an object, wherein at least one tomographic cross-sectional image is produced using a cross-sectional imaging method, in particular a magnetic resonance tomography method, wherein for a plurality of cross-sectional images of the same layer that are produced in a time-dependent manner, a measure of a detail, in particular the width of the boundary between two areas in at least one viewed direction is determined in a time-dependent manner. From the determined time-dependent measure, at least one time is determined for synchronizing and/or triggering a cross-sectional image capture device on a living organ, in particular the heart. The invention further relates to a cross-sectional image capture device designed to execute such a method.

15 Claims, 4 Drawing Sheets

QUANTIFICATION OF THE IMAGE QUALITY FOR THE MOTION-SYNCHRONIZED CAPTURE OF A CROSS-SECTIONAL TOMOGRAPHIC PICTURE OF AN OBJECT

CROSS REFERENCE TO RELATED APPLICATIONS

This application is the US-national stage of PCT application PCT/EP2010/001381 filed 5 Mar. 2010, published 10 Sep. 2010 as WO2010/099973, and claiming the priority of German patent application 102009011382.7 itself filed 5 Mar. 2009.

FIELD OF THE INVENTION

The invention relates to a method and an apparatus for the quantification of the image quality and/or the motion-synchronized capture of at least one tomographic picture of an object, wherein at least one tomographic cross-sectional image is produced using a cross-sectional imaging method.

BACKGROUND OF THE INVENTION

The method can preferably be used for the analysis and capture of cross-sectional images of an object, in particular a living object, that was captured by a magnetic-resonance tomography method. An apparatus according to the invention is preferably formed by a magnetic-resonance tomograph for spatially resolved nuclear magnetic-resonance measurement on a living object.

However, the invention is not limited to this concrete type of cross-sectional image capture but can basically be used for all techniques of cross-sectional image capturing that are technically available or still to be developed. Merely as examples can be mentioned: traditional x-ray tomography, computer tomography, positron emission tomography, electrical impedance tomography, neutron tomography, sonography etc. Moreover, the invention is not limited only to the medical field of use, but is preferably used there.

This method requires the existence of at least one cross-sectional picture that was produced using a cross-sectional imaging method, for example of the aforementioned type. In the meaning of the invention, a cross-sectional image is to be understood as a data set, in particular 2-dimensional data set of measurements, in particular intensity measurements. It is unimportant for the invention if this data set is actually illustrated as image. Preferably, the entire invention can work without illustration and only needs the data representing the cross-sectional image when carrying out the method.

The object and solution underlying the invention is explained in an exemplary and nonrestrictive manner by the technique of magnetic-resonance tomography (MRT).

Magnetic-resonance tomographs are generally known in the art and comprise substantially gradient coils for generating a plurality of in particular orthogonal magnetic fields, in particular in a Cartesian coordinate system, wherein usually a coil or coil arrangement is provided so as to generate a strong static magnetic field B0 along a Z-direction of a selected coordinate system, for example with field strengths of several Tesla. For this purpose, usually, superconducting coil arrangements are used.

Perpendicular and also parallel to the magnetic field direction B0 generated in this manner, moreover, further coils or coil arrangements are provided in order to generate magnet fields that are perpendicular to the static magnetic field and also at least one magnetic field that is parallel to this static magnetic field, wherein these magnetic fields are configured in particular as gradient magnetic fields, i.e., magnetic fields, the magnetic field strength of which changes over one of the coordinate axes. Through the interference it is achieved that the resonance frequency or the precession frequency of the spins changes depending on the spatially variable total magnetic field, whereby spatially resolved measurements can be implemented.

The measurement principle, in order to be able to achieve cross-sectional images in cross-section through living objects, is based on the fact that the spins, in particular hydrogen spins, of the living object initially align themselves within the static magnetic field B0 along the magnetic field direction and thus along the Z-axis.

By a high frequency excitation pulse that is adapted to the so-called Larmor frequency and is usually principally programmable with respect to the amplitude and the envelope, a deflection of the spins out of their equilibrium can take place so that the net magnetization Mz generated in the homogenous magnetic field B0 is deflected through the so-called flip angle so that a transverse magnetization component Mxy is present within the XY-plane of the selected coordinate system. Here, the flip angle depends substantially on the HF excitation pulse and is therefore programmable in an application-specific manner.

The transverse magnetization component Mxy generated in this manner is not temporally stable and due to different processes relaxes with different relaxation times, wherein the different processes superpose each other. These relaxations can be measured, in particular by receiving coils. The location of measurement is given by a volume element (voxel) of the object and is determined by a plurality of gradient magnetic fields that are at least temporarily superimposed on the static magnetic filed B0. Furthermore, it is known here to synchronize the start and/or preparation sequences of a measurement on a captured physiological motion.

These relaxation processes are known to the relevant person skilled in the art and are designated as T1-, T2- and T3-relaxation. Here, the T1-relaxation corresponds to the one at which the magnetization component Mxy flips back again in the direction of the Z-axis, whereas the T2-relaxation is based on a dephasing of the individual spins within the XY-plane and results in a weakening of the signal that is based on the emission of an electromagnetic wave due to the rotation of the transverse magnetization component in the XY-plane.

Furthermore, dephasings are superimposed on the T2-signal drop, which dephasings are given by macroscopic and microscopic magnetic field nonhomogeneities in the examined tissue or the examined object, which thus are based on differences in the magnetic susceptibility of the tissue. The effective relaxation rate, which includes T2-relaxation as well as susceptibility effects, is designated as T2* relaxation.

Besides the programming of at least temporarily acting gradient magnetic fields for achieving a spatial resolution in the examined object during the measuring preparation and/or signal reading, which is principally well known to the person skilled in the art, there are different possibilities to program so-called preparation and measuring sequences of pulses for controlling the respective coils (magnetic field coils and/or high frequency coils) so as to make T1-, T2- or T2*-relaxation times measured. In this context, this is also referred to as adequate weighting with respect to T1, T2 or T2* during the measurement acquisition.

With the possibility of spatially resolved measurements, 2-dimensional cross-sectional pictures through objects can be produced, wherein, correctly, such a picture represents at each pixel of the picture the signal from the respective volume element (voxel); thus, a cross-sectional image always represents not only an information of a mathematical plane, but also from a region extending in the layer thickness and perpendicular to the section. Such cross-sectional pictures, in turn, can be combined to form a 3-dimensional image.

The central challenges of magnetic-resonance (MR) imaging of the cardiovascular system include an unimpaired reproducibility, a spatial resolution in the millimeter range and in particular the imperative necessity of highly detailed geometrical imaging of the anatomy. In addition, a susceptibility-weighted MR presentation of the cardiovascular system requires imaging techniques that, with adequate effect, are able to reliably capture, present or quantify very small susceptibility-related differences between normal and abnormal tissue types in a diagnostically evaluatable manner.

High-quality MR illustration of moving organs requires the elimination of undesired influences due to breathing motion, heart motion, pulsation and blood flow. Therefore, the imaging has to be synchronized with the physiological motion or has to be adequately fast and thus immune with respect to the influences of motion.

Therefore, for an optimal illustration of moving organs, for example the freely movable heart, a compromise between short recording times and image quality has to be found. Short recording times can be implemented by a) ultrafast conventional imaging techniques, as b) parallel imaging as well as by c) accelerated imaging.

All these approaches for shortening the recording times can result in the improvement of insensitivity with respect to motion influences; however, at the same time, they cause significant deterioration in image quality and even nonusability of the images for diagnostic purposes.

The reason for this is speed increase-associated deterioration of the signal-to-noise ratio (SNR), the contrast-to-noise ratio (CNR) and also image interferences induced by fast, parallel and accelerated imaging, so-called artifacts, that can be introduced by the mentioned acceleration techniques. The development of the artifacts depends on the patients and the motion rate such as, e.g., heart frequency. In the image representation, these influences result in a widening of virtually real sharp boundary transitions between different areas of an object, in particular moving objects.

There are different approaches to implement quality control in the magnetic-resonance tomography. Test measurement with phantoms and test sequences allow to ensure the correct function of the magnetic-resonance tomograph and to assure constant measurement conditions. This test sequences that are to be repeated on a regular base check the function of the hardware.

Furthermore, in the clinical routine it is preferred to use only pulse sequences and protocols, the function of which has been sufficiently evaluated in advance. In order to evaluate the individual quality of a picture, there is the possibility to prospectively calculate the signal-to-noise ratio based on fundamental physical properties or to measure retrospectively. The signal-to-noise ratio reflects only a partial aspect of the perceived image quality and the exact determination of the signal-to-noise ratio is only possible with great difficulty.

Ultimately, up to now, the subjective experience of the physicians and user is necessary to evaluate the quality of the image data and thus decides if the images can be diagnostically used at a later time.

OBJECT OF THE INVENTION

It is the object of the invention to provide a method and an apparatus with which the quality of tomographic cross-sectional images can be automatically determined, in particular quantified.

Preferably, not only an objective determination of the image quality is to be carried out but also an automatic reaction on the capture of cross-sectional images has to be possible so as to be able to optimize the latter preferably in real time, in particular with respect to predetermined criteria. Preferably, it is also provided to provide a method with which the synchronization of the measuring data acquisition on the motion of organs can be carried out. In a preferred usage, the method and the apparatus are to be used to be able to capture the tomograph capture of the freely moving heart in a better, faster and more accurate manner.

SUMMARY OF THE INVENTION

The object is solved in that with a method for quantifying the image quality of at least one tomographic cross-sectional picture of an object and with which at least one tomographic cross-sectional image is recorded using a cross-sectional imaging method, in particular a magnetic-resonance tomography method, as a measure for the image quality in a cross-sectional image, an image detail of a boundary between two adjacent areas is measured, in particular with the signal intensity remaining constant in each case in such an area, in particular with the signal intensity remaining constant at least in predetermined or predeterminable boundaries. In a preferred embodiment, as such an image detail, the width of such a boundary can be determined.

The invention utilizes here that in case of a cross-sectional picture with a high image quality, the boundary between areas is sharper and thus more detailed or, with respect to the width, is narrower in a cross-sectional picture than in such a picture having a comparatively worse quality. Measuring an image detail of a boundary, in particular the width of the boundary between two areas in a cross-sectional picture thus results in information about the image quality, in particular in the sense that a more detailed or narrower boundary means a better image quality.

Measuring an image detail, for example the width between two areas, can take place mathematically based on the intensity measurements of which a cross-sectional picture is composed and that are given in dependence of the coordinates, in particular at least initially, the Cartesian coordinates. As already mentioned above, a concrete image representation is not necessary here, but it is sufficient according to the method to analyze the measurements that represent the cross-sectional picture. This applies basically to all steps when carrying out the method.

Furthermore, in a preferred embodiment, the principle of the measurement is based on the fact that two such adjacent areas in a cross-sectional picture are used that each and individually have a signal intensity that remains constant at least in predetermined or predeterminable boundaries with respect to the intensity measurements defining the area. Theoretically, in case of an ideally homogenous area, the intensity measurement should be the same everywhere within the entire area; however, this is actually not case. It is therefore preferably considered that the intensity measurements remain the same within boundaries. Such intensity measurements can be assigned with high probability to an area.

Furthermore, this preferably involves areas that have intensities that differ from each other, in particular greatly differ from each other in the intensity measurements so as to be able to capture such a boundary between the areas with a high probability. With respect to a concrete image representation of a cross-sectional recording, this can involve, e.g., a bright area and an adjacent dark area. A further preferred embodiment involves areas, the intensities of which differ from each other at least by a factor 2 of the standard deviation of the signal intensity of an area.

In a preferred usage, as areas, for example in case of a heart, the left ventricle is selected as one area and the myocardium surrounding the left ventricle is selected as another area. These two areas have very different signal intensities in a MRT cross-sectional picture, on the one hand due to the blood and on the other due to the muscle tissue. Accordingly, these areas are ideal for an analysis, in particular because specifically the heart is to be captured in preferred usage as cross-sectional picture and thus, according to the invention, the picture of the heart can be directly examined with respect to the quality.

A measurement for a detail, in particular the width of the boundary between two areas can be determined for example in units of a given physical or mathematical cross-sectional image resolution or real length units, wherein the image quality can be classified in at least two quality categories, depending on the determined measure.

Thus, by a selection or a plurality of selections of intensity measurements from all measurements of a cross-sectional picture or a region therefrom which, with respect to their coordinates (Cartesian or polar coordinates), extend over a boundary between two areas, it can be mathematically determined how wide this boundary is.

Preferably, for such an analysis, intensity measurements are selected that, within the plane of a cross-sectional image, lie on an (imaginary) straight line that intersects the boundary between the areas. Thus, it can be determined, for example, how many pixels (or voxels), or in general, how many length units the boundary region between the areas takes up in the cross-sectional image. The width obtained in this manner or the number of pixels or unit number represents a measurement for the width and at the same time for the image quality.

In another embodiment it can also be provided to determine as a measurement for the width, the gradient or quotient of the gradient of the intensity in the region of the boundary between the areas, for example in that preferably along the already mentioned straight line, the mathematical local derivative of the intensity measurements is determined or calculated at least in the boundary region.

Here, the algebraic sign of the gradient is not important, only the absolute value. The faster the absolute values of the intensity measurements change from the measurement that is typical for the first area to the measurement that is typical for the second area, the greater becomes the absolute value of the spatial gradient of the measurements and the smaller the quotient thereof. Thus, the quotient can represent a measurement for the width of the boundary region between the areas. The smaller the width or the absolute value of the quotient, the better the image.

The gradient itself or the absolute value thereof can be a direct measure for the image quality. The greater the absolute value of the gradient, the better is the image quality.

The width of the boundary between the two areas and thus a measure for the image quality can preferably be determined with the two above-mentioned method variants; however, the invention is not limited thereto. Any in particular mathematical method for determining a measurement for the width or another detail of the boundary and thus the image quality is comprised by the invention.

Once such a measure for the image quality has been determined for the image quality, then, for example depending on such a measure, a warning signal can be output, in particular for informing a user about an insufficient image quality. The user can stop the further image acquisition and restart with changed parameters, thereby saving valuable time.

It is particularly advantageous if in dependence of such a measure or the determined image quality or width, the image acquisition is automatically optimized, for example by automatically changing the input parameters, that influence the image capture, of a cross-sectional image capture apparatus, such as for example a MRT. Thus, according to the invention, such an apparatus can be calibrated and/or optimized in real time.

For example, an optimization can take place in such a manner that the speed of the image acquisition is increased until reaching a predetermined or predeterminable boundary of an image quality or width. This is based on the consideration that a slow image acquisition delivers a very good image quality, but, specifically in case of complex measuring series, takes too much time and in such a case, in particular during the examination of patients, is perceived by the latter as being unpleasant. In contrast, faster acquisitions often deliver a quality that is too poor. Thus, by the method according to the invention, a good compromise between speed and quality can be found, in particular automatically.

For the method according to the invention it is important according to a preferred embodiment that for analyzing a cross-sectional image or the intensity measurements thereof, those intensities that are present in the two underlying areas are known and thus are taken into account in the analysis. In order to achieve this it can be provided that automatically, the signal intensity in the first of the two adjacent areas is determined, in particular averaged over a plurality of intensity measurements within the first area, and the signal intensity in the second of the two adjacent areas is determined, in particular averaged over a plurality of intensity measurements within the second area. Thereby, information is available about the extreme intensity values that exist in the areas on both sides of the boundary between the areas.

It can then be provided that with the two determined signal intensities, an interval is defined that is divided into three equally sized subintervals, wherein in particular one of the middle subintervals, in particular the middle subinterval defines a transition region of intensities that are not assigned with sufficient probability to any of the two areas. Thus, it can be mathematically determined if intensity measurements that are read out from a cross-sectional image, in particular such intensity measurements having coordinates along a straight line intersecting the boundary, lie at a respective coordinate in one of the two areas or within the boundary region. The boundary region is specifically defined here in that the boundary region has intensities in one subinterval or, respectively, the subinterval formed in the middle. A check of the interval affiliation of the is measurements along the imaginary straight line, which check is performed along the straight line in a given resolution or step width, thus leads to the result how many steps are needed to pass through an interval, in particular the middle interval. The number of steps is then a measurement for the width of the boundary region and thus a measure for the image quality.

Alternatively, it can also be checked, in particular again along the mentioned straight line extending through the boundary, how great the gradient or quotient of the gradient of the intensity or, respectively, their respective absolute values is along this straight line. For this, again, by specifying the coordinates, the intensity measurements along this straight line can be read out from all measurements of a cross-sectional image or a region thereof, and for each or only individual measurements, the gradient at the respective coordinate can be formed. It is possible here, but not mandatory, to determine the gradient at each coordinate. It is sufficient to check first in which of the aforementioned subintervals the viewed intensity measurement is present. It is then possible, e.g., to perform the gradient formation only for such intensity measurements that lie in one of the middle subintervals or in the middle subinterval. If applicable, it is possible here to form only one gradient at the location of that intensity measurement that is furthest in the middle in the subinterval, or it is also possible to form a mean value from a plurality of gradients in one subinterval, in particular the middle subinterval.

Since the gradient or the absolute value thereof provides a measure of how fast the intensities change in the boundary region, such a gradient or also the quotient thereof forms a is measure either directly for the image quality or for the boundary width.

In order to carry out these method steps it is essential to provide the method with the areas or the coordinates or at least one respective coordinate of an area. Besides a principally possible manual selection of the areas or at least one of the areas in a representation of a cross-sectional image it is preferable according to the invention that when carrying out the method, the two adjacent areas or at least one of them are automatically localized in a cross-sectional image.

This can take place, e.g., in that in a cross-sectional image, a suitable or desired image region having two adjacent areas is automatically localized by pattern recognition. Specifically in the human anatomy, certain areas always have the same pattern such as, for example, ventricle and surrounding myocardial tissue. These concrete areas are represented in a MRT cross-sectional image, e.g., as almost circular disk-shaped bright surface (ventricle) that is surrounded by a dark circular frame (myocardial muscle) through full 360 degrees. Depending on the representation, these intensity conditions can also be inverted.

Such a pattern or also other patterns can be localized within a cross-sectional image by pattern recognition software. For example, through the pattern recognition, a central coordinate can be determined in at least one of the two areas, preferably the inner area, and can be made available for the further method.

In one possible configuration of the method it can then be provided that starting from a starting point, for example the central coordinate, in one of the two areas, the course of the signal intensity is captured in a (straight) direction toward the other area or is read out from the total of the measurements and is evaluated, and the signal intensity at the starting point or averaged over a region at the starting point defines the one interval boundary and the other interval boundary is given by an intensity value at a point that is located in the selected direction and has a low absolute value of the intensity gradient that, in the selected direction, follows a high absolute value of the intensity gradient.

Due to the consideration of the absolute values of the gradients without arithmetic sign it is irrelevant if the intensity in the viewed direction decreases or increases. If in the viewed direction, starting at the starting point in one area, a region is passed through in which the absolute value of the gradient first increases and then decreases and preferably remains constant in the range around zero, then it is ensured that the boundary region along the selected direction is passed through and that as the last measurement, a measurement in the other area is present.

The last measurement or an average from measurements in a spatial environment around the last measurement as well as the measurement at the starting point or the average from a plurality of measurements in an environment of the starting point thus can define the interval boundaries of the previously mentioned interval. If necessary, the interval boundaries can also be specified by a simple search of maximum and minimum out of all intensity values lying on the selected straight line.

Therefore, according to the invention, there is the possibility to automatically specify this interval. It is also possible to consider the respective algebraic sign instead of the absolute value of the gradient. The above-described check can is principally also be carried out between the areas in both opposite directions.

With knowledge of the intensity interval and the formation of the subintervals, the determination of the image quality can be performed in at least one straight direction in which the boundary is passed. Preferably, it can also be provided to perform the determination of a measure of an image detail, in particular the width for a cross-sectional image, in particular each cross-sectional image, in a plurality of radial directions that are in particular spaced at equispaced angles with respect to an origin that is placed in one of the two areas. This origin can be specified by the previously mentioned central coordinate. The results of the determination of the mentioned measurement of the respective directions can then be averaged over all selected directions so as to form a total result for a cross-sectional image.

Preferably, an origin from which all measurements of a detail or the width of the boundary is performed in different radial directions is placed in an area that is completely surrounded by the other area, in case of a cross-sectional image of a heart, is placed in particular in the ventricle that is surrounded by the myocardial muscle. Hereby it is achieved that in each radial direction, the boundary between both areas is passed through when carrying out the method.

When carrying out the method and reading out the intensity measurements from the measurements of a cross-sectional image along a straight line it is principally possible to use the measurements with Cartesian coordinates, in particular as is originally provided by a cross-sectional image capture apparatus.

In another method variant, which can be combined with all above-mentioned and below-mentioned steps, it can also be provided that the intensity measurements of a cross-sectional image that are given in dependence of Cartesian coordinates are converted, in particular for determining the width of a boundary or also for determining the synchronization times discussed below, into intensity measurements in dependence of polar coordinates, in particular angle and radius, with an origin that is placed into one of the areas, in particular into the area that is completely surrounded by another area, and in particular at the above-mentioned central coordinate. This simplifies substantially the calculations when carrying out the method.

According to another aspect of the invention, the object of the invention is also solved by a method for the motion-synchronized capture of at least one tomographic picture of an object, wherein at least one tomographic cross-sectional image is produced using a cross-sectional imaging method, in particular a magnetic-resonance tomographic method, wherein in particular principally all or individual method variants of the above-mentioned method variants can likewise be carried out, and wherein for a plurality of cross-sectional images of the same section that are recorded in a time-dependent manner, a measure for a detail, in particular the width of the boundary between two areas in at least one viewed direction is determined in a time-dependent manner, wherein from the determined time-dependent measure, at least one time is determined for synchronizing and/or triggering a cross-sectional image capture apparatus on a moving organ, in particular on a certain periodic motion phase of the moving organ and in is particular the heart. Here too, the measurement can preferably be determined in a plurality of particularly radial directions preferably spaced at equispaced angles, wherein in particular the respective results of each direction are averaged.

The method is based on the consideration that a motion, in particular an accelerated motion of an organ, for example of the heart between systole and diastole, results in a widening of the boundary between the two areas in the cross-sectional image, which widening is in particular time-dependent. In the cross-sectional images, a periodic motion such as the heart motion or breathing motion therefore causes a likewise periodic and time-dependent, for example breathing phase- or heart phase-dependent increase of the determined measure, in particular the determined width; this occurs in particular whenever the moving organ is maximally accelerated and/or is at maximum speed.

A time for synchronizing can be determined for example as the time, in particular of a periodic motion phase of a moving organ, at which the absolute value of the measure, in particular the width and/or the absolute value of the temporal gradient of the width, exceeds or falls below a predetermined limit value or, in case of a periodic behavior, reaches a maximum value.

Since due to the periodicity of the motion, the moving organ behaves always in the same way at this determined time, in particular the future image acquisition can be synchronized on these times so that high quality images with excellent detail sharpness can be obtained.

It is to be understood that the above-described methods can be used to analyze in one extreme case only a single cross-sectional image at a time and likewise, in the other extreme case, to analyze a multitude of tomographic cross-sectional images in a plurality of sections and time-dependent per each section.

If necessary, messages about each of the received results regarding time and/or the different layers can be provided.

The above-described methods according to the invention can particularly preferably be carried out by a data-processing system on which software for carrying out the described steps is implemented. To such software, at least the image data of a cross-sectional image, i.e. the intensity measurements in dependence of the image coordinates can be transferred as input variable. As a result, such software can provide the image quality or the boundary width as output parameter that in turn can form an input parameter for following methods such as, for example the optimization of the acquisition parameters of an apparatus for recording cross-sectional images.

Preferably, a data-processing system comprising such software can be integrated in a cross-sectional image capture apparatus so that this apparatus itself is capable of carrying out the method according to the invention.

The advantages of the invention as technical method are the simple and robust functionality as well as the possibility to measure and quantify the image quality by utilizing an objective evaluation criterion. An automatic evaluation of image data requires that a minimum in image quality is available. Thus, for an automated process, quality control is a decisive factor that previously always called for human interaction. It is difficult for inexperienced users to evaluate the image quality in a reliable and reproducible manner. The methods according to the invention allow a near-real-time control of the image quality. Examinations that experience an insufficient image quality, in particular for a diagnostic investigation to be carried out at a later time, can be detected in an automatic and fast manner so that the data acquisition can be stopped and new parameter settings can be performed so as to ensure the criteria of the desired or diagnostically needed image quality. Likewise, an acceleration of the data acquisition is possible if the image quality is well above average.

SPECIFIC DESCRIPTION OF THE INVENTION

Figure 1:
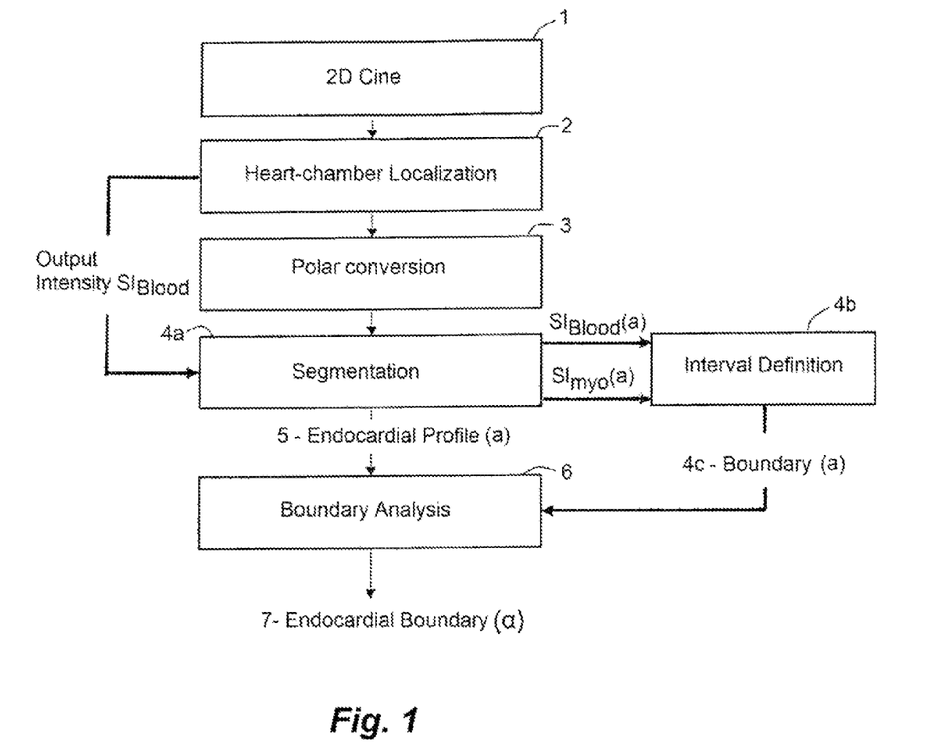
FIG. 1 is a schematic flow diagram for carrying out the method.
Figure 3:
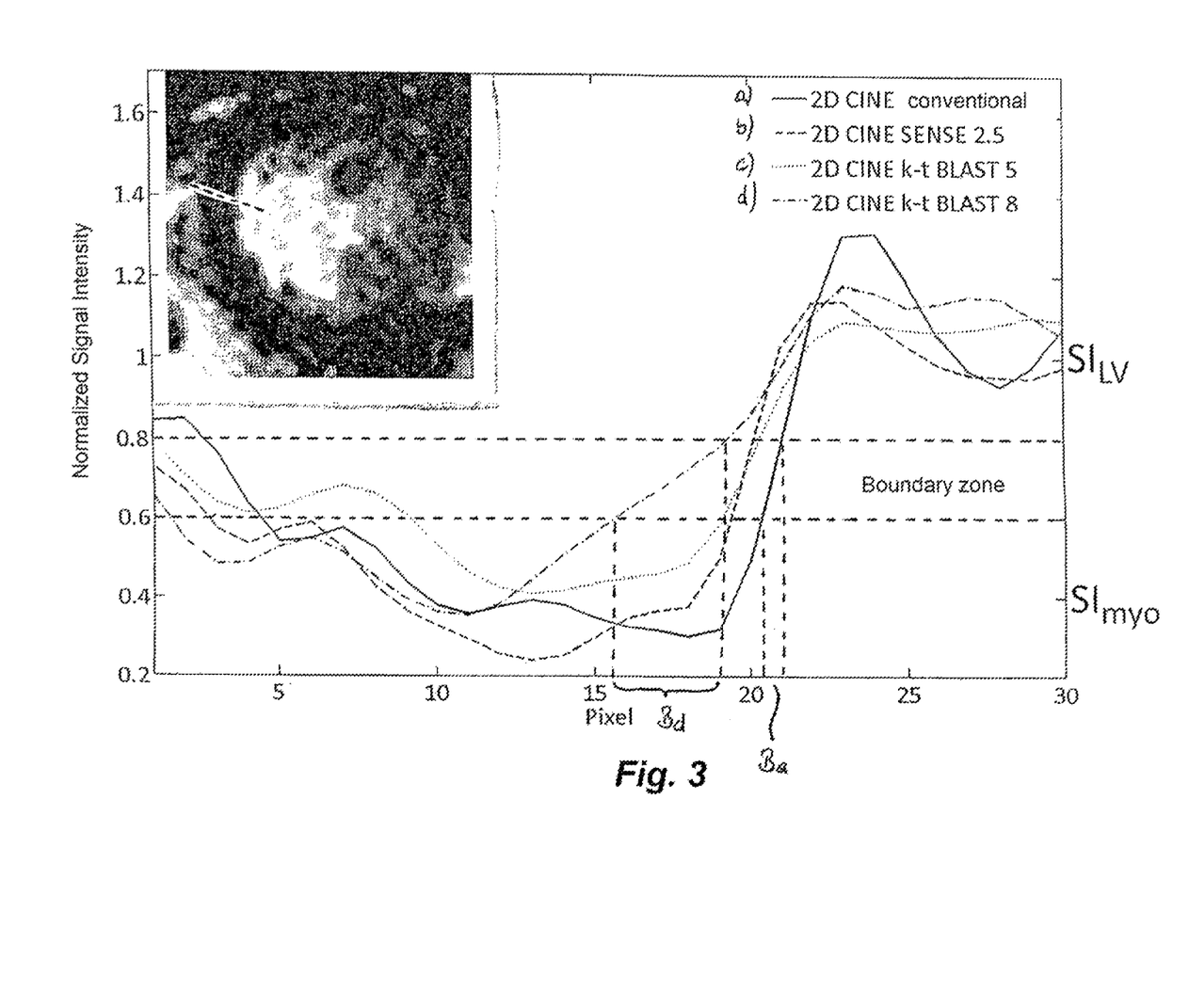
FIG. 3 illustrates the intensity curve during the transition from the left ventricle to the myocardial tissue for different acquisition techniques.

FIGS. 1 and 3 show the basic process flow of the method according to the invention for carrying out an image quality determination, here using the nonlimiting example of magnetic-resonance images of the moving heart that are produced as cross-sectional views in a magnetic-resonance tomograph.

Figure 2:
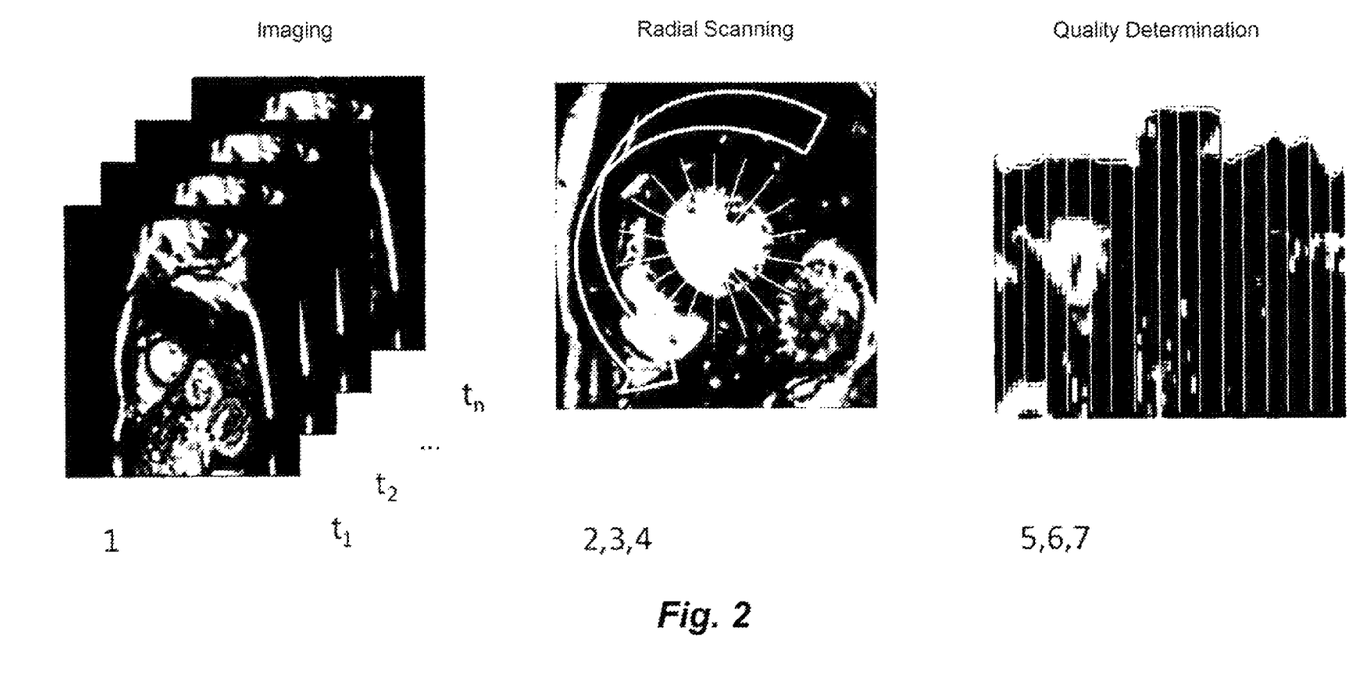
FIG. 2 illustrates the method based on cross-sectional images.

The individual steps of the method are indicated in FIGS. 1 and 2 with the same consecutive numbers 1 to 7.

According to the FIGS. 1 and 2, in step 1, a plurality of cross-sectional images of the same layer of the heart is taken at successive times t1, t2, . . . tn. This can be carried out using the so-called 2D-CINE method. Accordingly, the chronological sequence of such cross-sectional images can show a motion sequence of a moving organ, here shown using the example of the heart.

According to the invention at least one, preferably each of the cross-sectional images or the data representing such a cross-sectional image is processed using this method. Therefore, in a step 2, the localization of the ventricle as one of the two areas to be considered takes place, which can be carried out fully automatically based on a pattern recognition. For this purpose, the image data can be made available to software for pattern recognition. As a result of the pattern recognition, for example coordinates in the center of the ventricle can be reported back. These coordinates can then form the origin for a subsequent coordinate conversion in step 3 in which the measurements or image data that until then have been present as Cartesian coordinates are converted into measurements or image data in dependence of polar coordinates, whereby the further calculations are simplified.

FIG. 2 shows the left ventricle that was found by pattern recognition, where the origin is placed into the at least approximate center point of this ventricle, indicated here by straight lines radially extending from the origin. This left ventricle forms a first area for the method according to the invention and the myocardial tissue surrounding the ventricle forms the second area. The boundary between the areas is now measured according to the invention.

In step 4a, endocardial profiles are formed by reading is out the intensity measurements from the image data for each profile along respective straight lines that start from the origin and extend radially outward, preferably at equispaced angles, thereby intersecting the boundary region between ventricle and myocardial tissue.

The angular resolution can be any resolution and is illustrated in FIG. 2 in the middle view only as an example. Along this straight line, the intensity measurements are read at least from a region in the ventricle up to a region in the myocardial tissue, the direction of reading being irrelevant.

Preferably, the reading can begin in the area of the ventricle, preferably at the origin. The measurements are imported until it is ensured that the last measurement is to be assigned to the myocardial tissue. This can be determined based on the course of the absolute values of the intensities of the respective measurements, in particular taking into account the fact that the intensities in the region of the first area remain the same, at least within limits, and likewise in the second area; however, therebetween they can change significantly.

For example, by determining and evaluating the local gradient, the reading range can be determined, because starting from the origin and beginning with a small absolute value of the gradient and via a large absolute value of the gradient, a small one has to follow again. The coordinate boundaries of the endocardial profiles can also be determined by other methods and, where applicable, can be provided directly through the pattern recognition.

FIG. 2 shows in the right view the intensity curve of the individual endocardial profiles in a side-by-side representation plotted with respect to the angle. The upper part corresponds to the ventricle and the lower part to the myocardial tissue. Also plotted is the boundary determined and measured during the further process.

It should be noted here again that the image in FIG. 2 only serves for clarification of the invention and that to carry out the method imaging can be completely omitted. It is possible to carry out the method exclusively based on the measurements without providing them for image representation.

For each of the endocardial profiles, the minima and maxima of the intensity values are determined that, on the one hand, represent the intensity $SI_{Blood}(a)$ in the ventricle and, on the other, $SI_{myo}(a)$ in the myocardial tissue. Here, a is the angle of the viewed straight line or the profile in polar coordinates with respect to the defined origin.

If necessary, it is possible here to provide region-specific information for each of the two areas. With the values provided in this manner, the interval boundaries are defined and the obtained intensity interval is divided—in this case—in three equally sized subintervals. The middle subinterval describes the intensity values that lie within the boundary region between the two areas, thus between those values that can be clearly assigned to the ventricle or the myocardial tissue.

According to step 4c of FIG. 1, the boundary zone is defined in this manner with respect to the intensity values representing this boundary zone. This boundary zone is illustrated in a dashed line in FIG. 3 in a graphic representation of the signal intensity of a selected endocardial profile. The viewed profile involves the one that is represented in the image display as dashed line.

FIG. 3 shows (only for the purpose of comparison) for different image acquisition techniques a, b, c, d, the captured intensities of the viewed endocardial profile. The check according to step 6 of the captured intensity values of the profile, i.e. along the dashed straight line within the boundary zone, thus in the middle interval, and the information about the coordinates of these respective intensity values result according to the method in information about the width of the boundary between the areas and thus in information about the image quality according to step 7 of FIG. 1.

FIG. 3 clearly shows that with acquisition technique a, a width Ba in units of pixels, i.e. the image resolution, is achieved in the boundary zone; in contrast to that, with the (faster) acquisition technique d, a significantly larger width Bd is achieved. Thus, according to the method, an automatic message is received that with technique a, a higher image quality is achieved that, however, in the present case, is at the expense of the acquisition time due to the conventional acquisition technique. The width values B can be determined by simply forming the differences of the intensity values that, when running through the measurements, lie along the straight line on both borders of the middle interval.

The invention can be used to automatically change the acquisition parameters and, for example, depending on the determined image quality, switch to another acquisition technique or to select different parameters for the current technique so as to obtain an optimized compromise between image quality and acquisition speed.

Figure 4:
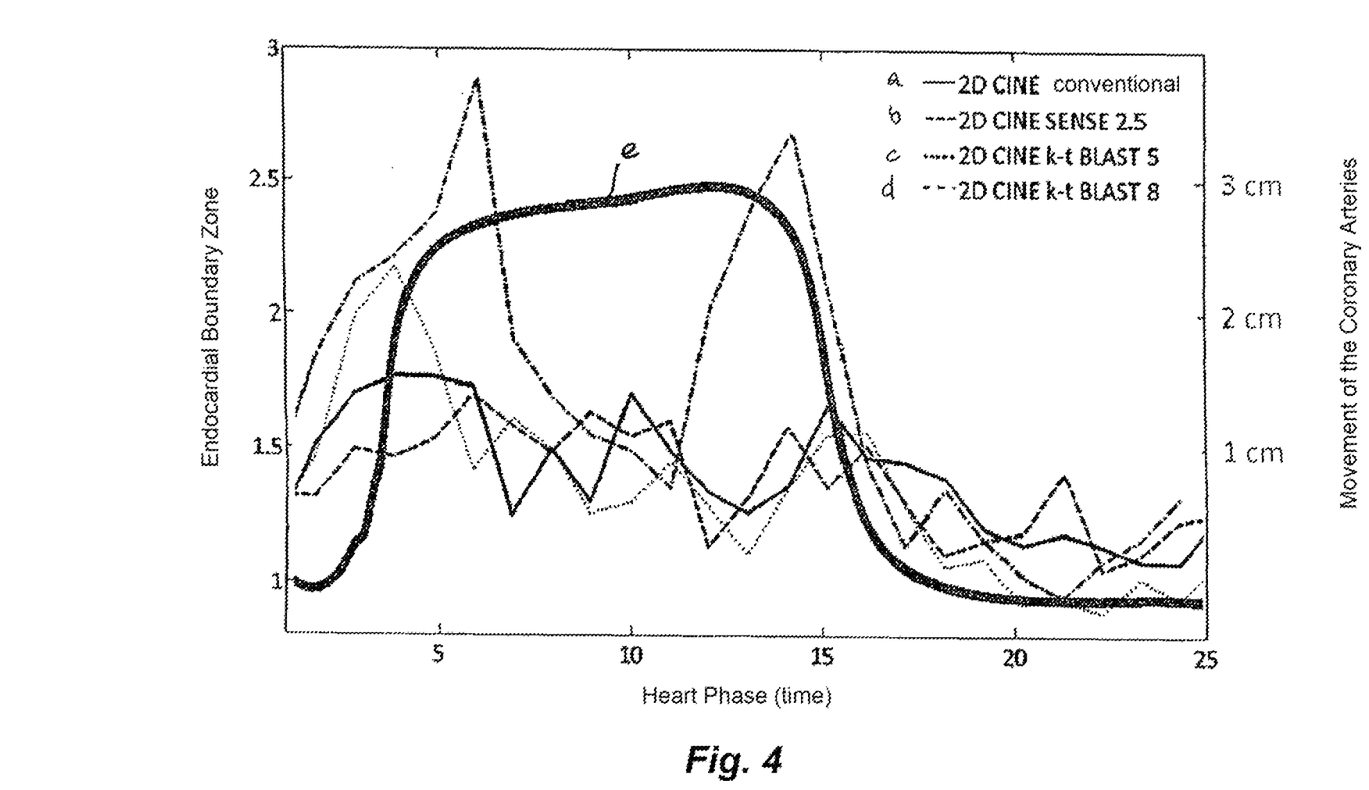
FIG. 4 illustrates the determined boundary widths as a function of the temporal heart phase and, in comparison, as a function of the motion of the coronary artery

FIG. 4 shows in another illustration the endocardial boundary width—determined as described above—in particular in units of the image resolution and as a function of time, here as a function of the temporal heart phases during the free motion of the heart, and in each case for the different acquisition techniques a to d for the purpose of comparison.

These time-dependent boundary widths can be determined in that the same step is recorded in a time-dependent manner and for each chronological step, the aforementioned analysis is carried out, in particular with the image acquisition technique and the parameters remaining the same. Here, it is possible to determine the boundary width in each case only for one endocardial profile or averaged over a plurality of profiles per section.

It is shown here that at least for some acquisition techniques, and in particular for the fastest one, it applies that the determined endocardial boundary width shows a clear dependence on time, i.e., here, the heart phase. A comparison with the temporal position displacement of the coronary artery according to line e shows that significant increases of the boundary width correlate in terms of time with the position displacement of the coronary artery that results from the transmission of the contraction or relaxation of the heart. The illustrated curve of the position displacement that represents the phase of maximum contraction (systole) and the resting phase of the heart or phase of maximum filling of the myocardial muscle (diastole) in a known manner shows that the detected time-dependent boundary width is synchronous to systole and diastole or, respectively, the transition areas.

Thus, according to the invention, a signal for triggering or synchronizing the image acquisition of an MRT tomograph on the heart motion can be determined from the temporal course of the boundary width. A trigger or synchronization signal can be outputted for example at a time of occurrence of a maximum of the boundary width or the highest temporal gradient of the boundary width, or on exceeding a predetermined threshold of these variables.

For example, during a continuous image acquisition one can determine the times of triggering or synchronizing in the described manner and subsequently continuously shift the times of acquisition in the phase, i.e. temporally, based on the obtained information about the synchronization times.

With the invention, a technical method is provided for to objective boundary-width determination over portions or even the entire cardiac cycle. Thus, influences of motion affecting the image quality can be detected or the state of motion of the heart or phases of strong contraction or relaxation of the myocardial muscle can be identified as shown in FIG. 4.

Thus, through the motion analysis, noninvasive monitoring of the cardiac condition during image acquisition is possible.

The results of the automatic boundary-width analysis can be used to retrospectively or in real-time adjust the imaging parameters so as to achieve a better image quality or, if necessary, to accelerate the imaging so as to minimize the influence of motion. For this purpose, the reconstructed image data are analyzed and the image quality is quantified on the basis of the described objective metric on the boundary width of the cardiac wall borders.

If the boundary-width determination finds the image is quality to be very good, in addition, acceleration techniques can be used so as to optimize the ratio of examination time to image quality. In this manner it is possible under online control of the image quality to automatically exhaust the existing acceleration techniques individually via boundary-width determination.

Besides optimizing the time-quality ratio, the invention also allows reliable quality control of the image data that ensures that no diagnostically unusable image data are used for a diagnosis subsequent to the image acquisition. In case of an insufficient image quality, the automatic analysis allows a direct repetition of the imaging.

Besides monitoring and optimizing the image quality via a direct automatic analysis during the image acquisition process, the invention also allows reliable quality control of the image data, in particular as input criteria that ensures that after the image acquisition, no diagnostically unusable image data are used for a further image evaluation and diagnosis in particular by software implemented on a data-processing system, in particular software for quantifying the left ventricular function of the heart, to which software at least the image data of a cross-sectional image are transferred as input variable.

The invention has the advantage that specifically diagnostically relevant image details can be analyzed and the quality in particular of heart MRT image data can be evaluated and quantified in a reliable and robust manner. Thus, all image quality-influencing factors, from intrinsic physical properties to patient-related factors, are considered. The quality analysis is not only based on previously primarily used global image properties such as, for example signal-to-noise ratio or contrast-to-noise ratio, but operates on the detail level of the image data.

This way, the results of the automatic analysis correspond with the results of the subjective evaluation by experienced physicians or other users. With this technical method it is now possible to measure image quality that up to now is perceived and evaluated subjectively by users and physicians in an objective manner and to utilize the result for image quality control or for ensuring a predefined image quality.

In addition, the analysis of the cardiac wall borders allows evaluation of the motion of the heart because the cardiac wall borders are monitored. This means a technical method is available here with which image data can be assigned to the heart cycle or to phases of strong heart motion. Conversely, the method therefore also allows the synchronization of the imaging with the heart cycle.

The invention claimed is:

1. A method for the quantification of the image quality of at least one tomographic picture of an object, the method comprising the steps of:
   recording at least one tomographic cross-sectional image using cross-sectional magnetic-resonance imaging;
   determining, as measure for the image quality in a cross-sectional image, the width of a boundary between two adjacent areas in which the signal intensity is constant at least within predetermined or predeterminable boundaries;
   determining a signal intensity in the first of the two adjacent areas automatically;
   averaging the determined signal intensity over a plurality of intensity measurements within the first area;
   averaging a signal intensity in the second of the two adjacent areas over a plurality of intensity measurements within the second area; and
   defining with the two determined signal intensities an interval that is divided into three equally sized subintervals of which the middle subinterval defines a transition region of intensities that are not assigned to any of the two areas.

2. The method according to claim 1, further comprising the step of:
   recording a multitude of tomographic cross-sectional images in a plurality of layers and per each layer in a time-dependent manner, and
   determining the width for each of the layer images at a plurality of positions of a boundary.

3. The method according to claim 1, further comprising:
   determining a measurement for the width in units of a given physical or mathematical cross-sectional image resolution and,
   depending on the determined measurement, classifying the image quality in at least two quality categories.

4. The method according to claim 1, further comprising the step of:
   determining a measurement for the width as quotient of the gradient of the intensity in the region of the boundary between the areas.

5. The method according to claim 1, further comprising the step of,
   depending on a determined image quality or width, generating a warning signal for informing a user about an insufficient image quality.

6. The method according to claim 1, further comprising the step of,
   depending on a determined image quality or width, changing the input parameters of a cross-sectional image capture apparatus influencing the image acquisition.

7. The method according to claim 6, further comprising the step of:
   increasing a speed of the image acquisition until a predetermined or predeterminable boundary of an image quality or width is reached.

8. The method according to claim 1, further comprising the step of:
   automatically localizing in a layer image a suitable or desired image region with two adjacent areas by a pattern recognition.

9. The method according to claim 1, further comprising the step of:
   capturing and evaluating starting from a starting point in one of the two areas the course of the signal intensity in the direction toward the other area such that the signal intensity at the starting point or averaged over a region at the starting point defines the one interval boundary and the other interval boundary is given by an intensity value at a point located in the selected direction and has a low absolute value of the intensity gradient that, in the selected direction, follows a high absolute value of the intensity gradient.

10. The method according to claim 1, further comprising for determining the width of the boundary between the areas the steps of:

either determining over how many steps of a predetermined or predeterminable mathematical or physical cross-sectional image resolution the intensity measurements viewed in a direction from one to the other area and across the boundary lie within the middle interval or determining how great the gradient or quotient of the gradient of the intensity is in the middle interval at the local positions that have intensities that lie in the middle interval.

11. The method according to claim 10, further comprising the step of:

determining the width for a cross-sectional image for each cross-sectional image in a plurality of radial directions that are at equispaced angles with respect to an origin that is within one of the two areas.

12. The method according to claim 11, further comprising the step of:

placing the origin in an area that is completely surrounded by the other area, and in case of a cross-sectional image of a heart in the ventricle that is surrounded by the myocardial muscle.

13. A method for the quantification of the image quality of at least one tomographic picture of an object, the method comprising the steps of:

to recording at least one tomographic cross-sectional image using cross-sectional magnetic-resonance imaging;

determining, as measure for the image quality in a cross-sectional image, the width of a boundary between two adjacent areas in which the signal intensity is constant at least within predetermined or predeterminable boundaries; and converting the intensity measurements of a cross-sectional image that are given in dependence of Cartesian is coordinates for determining the width of a boundary into intensity measurements in dependence of polar coordinates with an origin that is within one of the areas that is completely surrounded by another area.

14. A method for the quantification of the image quality of at least one tomographic picture of an object, the method comprising the steps of:

recording at least one tomographic cross-sectional image using cross-sectional magnetic-resonance imaging;

determining, as measure for the image quality in a cross-sectional image, the width of a boundary between two adjacent areas in which the signal intensity is constant at least within predetermined or predeterminable boundaries;

determining for a plurality of cross-sectional images of the same layer that are recorded in a time-dependent manner, the width of the boundary between two areas in at least one viewed direction in a time-dependent manner;

determining from the determined time-dependent measure at least one time for synchronizing or triggering a cross-sectional image capture apparatus on a moving organ; and determining the time as that time of a periodic motion phase of a moving organ, at which the absolute value of the width or the absolute value of the temporal gradient of the width, exceeds or falls below a predetermined limit value or assumes an extreme value.

15. The method according to claim 1, wherein the method is carried out by software implemented on a data-processing system, to which software at least the image data of a cross-sectional image is transferred as input variable.

* * * * *